(12) United States Patent
Chachques et al.

(10) Patent No.: US 10,004,602 B2
(45) Date of Patent: Jun. 26, 2018

(54) BIOACTIVE IMPLANT FOR MYOCARDIAL REGENERATION AND VENTRICULAR CHAMBER RESTORATION

(71) Applicants: INSTITUT QUIMIC DE SARRIA, Barcelona (ES); UNIVERSITAD POLITECNICA DE VALENCIA, Valencia (ES); FUNDACIO GERMANS TRIAS PUJOL, Badalona (ES); ASSOCIATION CARDIO-MONDE, Paris (FR)

(72) Inventors: Juan Carlos Chachques, Paris (FR); Antonio Bayes Genis, Principal (ES); Manuel Monleon Pradas, Valencia (ES); Carlos Eduardo Semino, Barcelona (ES); Philippe Jenny, Pessac (FR)

(73) Assignees: INSTITUT QUIMIC DE SARRIA, Barcelona (ES); UNIVERSIDAD POLITECNICA VALENCIA, Valencia (ES); FUNDACION GERMANS TRIAS PUJOL, Badalona (ES); ASSOCIATION CARDIO-MONDE, Paris (FR)

( * ) Notice: Subject to any disclaimer, the term of this patent is extended or adjusted under 35 U.S.C. 154(b) by 0 days. days.

(21) Appl. No.: 15/162,492

(22) Filed: May 23, 2016

(65) Prior Publication Data

US 2016/0331535 A1    Nov. 17, 2016

Related U.S. Application Data

(60) Division of application No. 14/600,583, filed on Jan. 20, 2015, which is a division of application No.
(Continued)

(30) Foreign Application Priority Data

Jul. 30, 2010   (EP) .................................... 10305851

(51) Int. Cl.
*A61F 2/24* (2006.01)
*A61L 27/26* (2006.01)
(Continued)

(52) U.S. Cl.
CPC .......... *A61F 2/2481* (2013.01); *A61F 2/0077* (2013.01); *A61F 2/24* (2013.01);
(Continued)

(58) Field of Classification Search
CPC .................................. A61F 13/00; A61F 2/24
(Continued)

(56) References Cited

U.S. PATENT DOCUMENTS 5,634,895 A * 6/1997 Igo ........................ A61M 25/10
604/20
6,592,369 B2 7/2003 Sun et al.
(Continued)

OTHER PUBLICATIONS

Boublik et al., "Mechanical Properties and Remodeling of Hybrid Cardiac Constructs Made from Heart Cells, Fibrin, and Biodegradable, Elastomeric Knitted Fabric", 11(7/8):1122-1134.

*Primary Examiner* — Yashita Sharma
(74) *Attorney, Agent, or Firm* — Porzio Bromber & Newman P.C.

(57) ABSTRACT

Bioactive implant for myocardial regeneration and ventricular chamber support including an elastomeric microporous membrane. The elastomeric microporous membrane being at least one non-degradable polymer and at least one partially degradable polymer. The non-degradable polymer is selected from polyethylacrylate and polyethylacrylate copolymerized with a hydroxyethylacrylate comonomer. The partially degradable polymer is selected from caprolactone 2-(methacryloyloxy)ethyl ester and caprolactone 2-(methacryloyloxy)ethyl ester copolymerized with ethylacrylate. The elastomeric microporous membrane further includes a nanofiber hydrogel, and cells. The bioactive implant, having (Continued)

one or two helical loops, contributes to the restoration of the heart conical shape. Cardiac wrapping by ventricular support bioprostheses of the present invention, having reinforcement bands spatially distributed as helicoids, recovers the sequential contraction of the myocardium resulting in the successive shortening and lengthening of the ventricles, therefore improving the ejection (systolic function) and suction of blood (diastolic function).

17 Claims, 9 Drawing Sheets

Related U.S. Application Data

13/660,086, filed on Oct. 25, 2012, now Pat. No. 8,968,417, which is a continuation-in-part of application No. PCT/EP2011/056576, filed on Apr. 26, 2011.

(60) Provisional application No. 61/327,864, filed on Apr. 26, 2010.

(51) Int. Cl.
| | | |
|---|---|---|
| A61L 27/38 | (2006.01) | |
| A61L 27/52 | (2006.01) | |
| A61L 27/54 | (2006.01) | |
| A61L 27/56 | (2006.01) | |
| A61F 2/00 | (2006.01) | |
| A61L 27/58 | (2006.01) | |
| C12N 5/077 | (2010.01) | |
| C12N 5/0775 | (2010.01) | |
| A61L 27/16 | (2006.01) | |
| A61L 27/24 | (2006.01) | |

(52) U.S. Cl.
CPC ............... *A61L 27/16* (2013.01); *A61L 27/24* (2013.01); *A61L 27/26* (2013.01); *A61L 27/3834* (2013.01); *A61L 27/3839* (2013.01); *A61L 27/3873* (2013.01); *A61L 27/52* (2013.01); *A61L 27/54* (2013.01); *A61L 27/56* (2013.01); *A61L 27/58* (2013.01); *C12N 5/0657* (2013.01); *C12N 5/0663* (2013.01); *C12N 5/0667* (2013.01); *A61F 2002/0081* (2013.01); *A61F 2210/0004* (2013.01); *A61F 2210/0057* (2013.01); *A61F 2220/0008* (2013.01); *A61F 2220/0016* (2013.01); *A61F 2240/001* (2013.01); *A61L 2300/252* (2013.01); *A61L 2300/44* (2013.01); *A61L 2300/442* (2013.01); *A61L 2300/602* (2013.01); *A61L 2400/12* (2013.01); *A61L 2430/20* (2013.01); *C12N 2513/00* (2013.01); *C12N 2533/30* (2013.01)

(58) Field of Classification Search
USPC ......... 623/13.17, 13.18, 14.12, 14.13, 15.11, 623/15.12, 23.57–23.59, 23.72–23.76; 606/151–158; 604/500–522; 424/422–437; 521/61–64
See application file for complete search history.

(56) References Cited

U.S. PATENT DOCUMENTS

| | | |
|---|---|---|
| 7,659,219 B2 | 2/2010 | Biran et al. |
| 8,301,233 B2 | 10/2012 | Zhang et al. |
| 2002/0004542 A1 | 1/2002 | Ogoe |
| 2002/0061493 A1 | 5/2002 | Sun et al. |
| 2006/0189840 A1 | 8/2006 | Walsh |
| 2007/0082021 A1 | 4/2007 | Bates |
| 2008/0208167 A1 | 8/2008 | Stankus |
| 2008/0254002 A1 | 10/2008 | Edelberg et al. |
| 2008/0293072 A1 | 11/2008 | Dertinger |
| 2011/0202142 A1 | 8/2011 | Mao et al. |

* cited by examiner

BIOACTIVE IMPLANT FOR MYOCARDIAL REGENERATION AND VENTRICULAR CHAMBER RESTORATION

CROSS REFERENCE TO RELATED APPLICATION

This application is a continuation-in-part of PCT/EP2011/056576, filed 26 Apr. 2011, which claims the benefit of U.S. Provisional Patent Application No. 61/327,864 filed 26 Apr. 2010 and EP 10305851.7 filed 30 Jul. 2010, the entirety of which applications are hereby incorporated by reference into this application.

The present invention generally relates to the field of myocardial repair, more particularly to a method and to a bioactive implant for repairing myocardium and support ventricular chamber configuration and function.

BACKGROUND OF THE INVENTION

Heart failure (HF) is primarily a condition of the elderly, and thus the widely recognized "aging of the population" contributes to the increasing incidence of HF. The incidence of HF approaches 10 per 1000 population after age 65 and approximately 80% of patients hospitalized with HF are more than 65 years old.

Heart failure is a major and growing public health problem in the developed countries. In the United States approximately 7 million patients have HF, and more than 550 000 patients are diagnosed with HF for the first time each year. The disorder is the primary reason for 12 to 15 million office visits and 6.5 million hospital days each year.

Heart failure is the most common Medicare diagnosis-related group (i.e., hospital discharge diagnosis), and more Medicare dollars are spent for the diagnosis and treatment of HF than for any other diagnosis.

In Europe, the epidemiology is not well known; it is estimated that about 30 millions patients suffer from heart failure.

Cell transplantation and tissue engineering to the diseased heart are emerging as promising strategies to prevent or to treat refractory heart failure that cannot successfully be treated by conventional therapies. The advances in cellular biology, in biological engineering and nanotechnologies give further advances in this option. Implanting exogenous cells supported by scaffolds in the myocardial scar tissue to replace the damaged or the disabled cells is a safe and efficient therapeutic approach.

Stem Cell Niche and Cell Homing

After myocardial infarction, not only the changes affect the contractile element of the myocardium (cardiomyocytes) but also the extracellular matrix. The collagen type I percentage decreases from 80% to 40%, this collagen is responsible with the other elements of the heart muscle of the normal ventricular geometry.

The efficiency of cell therapy to augment recovery after myocardial ischemia depends on the sufficient recruitment of applied cells to the target tissue. Homing to sites of active neovascularization is a complex process depending on a timely and spatially orchestrated interplay between chemokines (e.g. SDF-1), chemokine receptors, intracellular signalling, adhesion molecules (selectins and integrins) and proteases.

Until now, cell transplantation for cardiac support and regeneration was limited by poor effects in ventricular function. This can be due to the lack of gap junctions between the native myocardium and the grafted cells. Also, cell transplantation seems to be limited by the relocation of transplanted cells to remote organs and noninfarcted myocardium and by the death of transplanted cells. Most cell death occurs in the first few days post-transplantation, likely from a combination of ischemia, apoptosis and inflammation. Apoptosis can be induced by anchorage-dependent cells detaching from the surrounding extracellular matrix.

The cell niche, a specialized environment surrounding stem cells, provides crucial support needed for cell maintenance. Compromised niche function may lead to the selection of stem cells that no longer depend on self-renewal factors produced by its environment. Strategies for improving cell survival and differentiation such as tissue engineering, has been developed.

Cardiac Tissue Engineering

Extra cellular matrix remodeling in heart failure (excessive matrix degradation and myocardial fibrosis) contributes to Left Ventricular (LV) dilatation and progressive cardiac dysfunction. Myocardial tissue engineering should provide structural support to the heart, specific scaffolds should help to normalize cardiac wall stress in injured regions improving strain distribution. Engineering materials requiring specific properties of stiffness and resistance to deformation can be implanted or seeded into the myocardial tissue. They are composed of natural or synthetic structure capable of supporting 3D tissue formation. Survival and engraftment of cells within the environment of the ischemic myocardium represents a challenge for all types of cells, regardless of their state of differentiation. Scaffolds characteristics are critical to recapitulating the in vivo milieu and allowing cells to influence their own microenvironments. Such scaffolds serve at least one of the following purposes: allow cell attachment and migration, deliver and retain cells and biochemical factors, enable diffusion of vital cell nutrients and expressed products, and exert certain mechanical and biological influences to modify the behavior of the cell phase. In addition, development of gap junctions within the new created tissue as well as with the host myocardial tissue are of great functional interest.

Ventricular Chamber Restoration

Restoration of ventricular shape and geometry is a surgical procedure designed to restore or remodel the left and/or right ventricle to its normal, conical shape and size in patients with akinetic segments of the heart, secondary to either post infarction cardiomyopathy or dilated cardiomyopathy. The restoration procedure can be performed during or after coronary artery bypass grafting (CABG), mitral valve repair or replacement and other procedures such as implantation of stem cells for myocardial regeneration. Surgical ventricular restoration has been performed: 1) by partial resection of the ventricular wall using cardiac arrest and cardiopulmonary bypass (extracorporeal circulation), or 2) by external ventricular remodelling, e.g. cardiac wrapping with autologous tissues like the latissimus dorsi muscle flap. Ventricular restoration procedure with bioactive implants avoids cardiac arrest and extracorporeal circulation.

Ventricular Restraint Therapies

Heart failure patients develop oversized, dilated hearts due to increased filling pressures. Over time the increased workload of the heart can lead to a change called remodeling, which is the enlargement and thinning of the ventricles. The failing cardiac muscle need to be supported to decrease the ventricular wall stress. Mesh wrap devices that are implanted around the heart have been used. These devices are intended to prevent and reverse the progression of heart failure by improving the heart's structure and function, leading to improvements in the survival and quality of patient's life. For example, implantable devices have been tested for ventricular restraint therapy, like polyester netlike sack designed for placement around the heart fabricated into a multifilament mesh knit (CorCap device, Acorn). Also a nitinol mesh for ventricular wrapping was investigated (HeartNet device, Paracor). Permanent implantation experience of both devices showed adverse effects like restriction in diastolic function and lack of improvement of systolic function, without evidence of myocardial healing. These results have limited its large clinical application, including the "not to approve" U.S. Food and Drug Administration (FDA) decision.

Translational Research

Experimental and clinical studies have been performed on stem cell therapy and tissue engineered approaches for myocardial support and regeneration. The results of these investigations tend to demonstrate the interest of simultaneous intrainfarct stem cell therapy with the fixation of cell-seeded matrices onto the epicardium of infarcted ventricles.

Experimental studies suggest that simultaneous autologous intramyocardial injection of stem cells and fixation of a cell-seeded collagen matrix onto the epicardium is feasible. However, the long-term efficacy of this approach is compromised by the complete biodegradation of the grafted collagen matrix.

WO2006/036826 discloses a tissue-engineering scaffold containing self-assembled-peptide hydrogels.

US2005/0095268 describes a cardiac wall tension relief with cell loss management.

The article of Boublik et al. (Tissue engineering, 2005) relates to the mechanical properties and remodelling of hybrid cardiac constructs made from heart cells, fibrin, and biodegradable, elastomeric knitted fabric.

In summary, the following problems are encountered in the field of myocardial repair.

1) It is difficult to repair a large myocardial scar.
2) Cell bio-retention and engraftment within scar tissue is too low.
3) Mortality of implanted cells in ischemic myocardium is high.
4) Extracellular matrix remodeling in ischemic heart disease (excessive matrix degradation and myocardial fibrosis) contributes to LV dilatation and progressive cardiac dysfunction.
5) The therapeutic limitation of heart dilatation and the recovery of the native elliptical shape of ventricular chambers are key prognostic factors for survival in HF patients.
6) In cell transplantation, survival and engraftment within the environment of the ischemic myocardium represents a challenge for all types of cells, regardless of their state of differentiation.
7) Up to now, the optimal cell-matrix combination for robust and sustained myocardial restoration has not been identified.
8) The long-term efficacy of the approach—autologous intramyocardial injection of stem cells and fixation of a cell-seeded collagen matrix onto the epicardium—is compromised by the complete biodegradation of the grafted collagen matrix.
9) There are undesired effects of growth factor administration.
10) Tissue viability/evolution over time.

SUMMARY OF THE INVENTION

The present invention provides a bioactive implant for repairing myocardium and support ventricular chamber configuration and function, and a method for preparing such implant. The bioactive implant is grafted onto and/or into the ventricular wall for myocardial regeneration, for left or right ventricular support and to restore the elliptical shape of ventricular chambers.

The scaffolds are created by the combination of a membrane which is a mix of biodegradable materials (biological or synthetic) with non-biodegradable (biostable) synthetic materials, with hydrogel and cells. During the procedure, cells, e.g. stem cells mixed with hydrogel, are seeded into/onto the membrane, i.e. a template form, and immediately or secondarily grafted onto diseased myocardial tissue.

The method of the invention comprises the steps of creating a scaffold combining biodegradable with non-biodegradable materials, obtaining autologous cells or cells from a donor, implanting the cells into the matrix and grafting the composite cellular scaffolds onto the heart.

The implant and method of the present invention aims to improve ventricular function, to limit chronic dilation of ventricular chambers and to restore the native elliptical shape of the heart as a new modality in the treatment of heart failure.

The advantages of the objects of the present invention are the following:

a) Stem cell transplantation induces myocardial angiogenic and/or myogenesis improving myocardial viability and reducing scar fibrosis.

b) Matrix scaffolds grafting improves stem cell niche and cell homing, consequently increasing the thickness of the infarct scar with viable tissues. This composite material helps to normalize cardiac wall stress in injured regions. In addition, new vessels formation from the epicardium and from the surrounding well irrigated myocardium contribute to the reduction of the fibrosis and size of infarction scars, inducing the regeneration of contracting cells and extracellular collagen matrix.

c) Synthetic cardiac support material onto the heart brings long-term beneficial impact on ventricular chamber size and shape reducing tension and promoting limitation of adverse remodelling. In addition, this material helps to normalize cardiac wall stress in injured regions improving strain distribution, avoiding scar dyskinesia and the risk of formation of ventricular aneurysms, ventricular wall rupture and mitral valve insufficiency.

d) Adapted ventricular wrapping. The bioactive implants of the present invention are designed for left ventricular and/or right ventricular support and regeneration, including different sizes for partial or complete ventricular wrappings. The implant characteristics (mechanical, physical, chemical, biological) are adapted for the left or the right ventricle geometry, physiology and pathology.

e) Maintenance and survival of the implanted cells in situ. Preparation and maintenance of the cellular population of the bioactive implants is obtained by cardiac cell therapy before, during or after grafting "Bioactive Implants" onto the heart. Cell transplantation is performed using either catheter-based approaches via the endocardium (endoventricular), via an intravascular procedure (through coronary arteries or veins) or injecting the cells through the epicardium during cardio-thoracic surgery, thoracoscopy or computer-robotic assisted procedures. Additionally, lowered oxygen tension (e.g., 5% to 15%) is used during cell growth as a preconditioning procedure to improve cell survival following patch implantation in ischemic myocardium.

f) Prevention of LV dilatation and progressive cardiac dysfunction. According to an aspect of the invention, the entire organ is contained with the elastomeric membrane of the bioactive implant to prevent heart dilatation. Thus, with decreased ventricular wall tension the complementary treatment of grafting biological tissue (e.g. peptides and stem cells) can successfully achieve myocardial regeneration. Additionally, pacing electrodes can be used in the method of the invention and also incorporated into the Bioactive Implants and the native myocardium for synchronous electrostimulation of the implanted tissue and other electrophysiological treatments (defibrillation, resynchronization, etc).

g) Regenerative treatment in association with implants in view of survival and engraftment. Cell-based myocardial regenerative treatments can be associated, i.e. intramyocardial and intrainfarct stem cell transplantation, with the implantation of bioactive implants onto the heart. Associated method for seeding or implanting stem cells into or onto the Bioactive Implants using the following methods: mechanical (shaking, centrifugation), chemical (electrophoresis), physical (electroporation), etc. Seeded or implanted cells that can be angiogenic, cardio-myogenic or pluripotents. Additionally, Bioactive Implants can be labelled with products (dies, microspheres, radioisotopes, iron-particles, etc) for evaluation of biodegradation, integration, proliferation, differentiation and function, using radiologic, ultrasound-echocardiographic, radioisotopic, metabolic (PET), RMI, CT Scan and bio-luminescence-fluorescence methods (etc.).

h) Adjusted composition of the bioactive implants. The composition of the bioactive implants has a percentage of non-biodegradable (synthetic) versus biodegradable (biological or synthetic) components, which ranges from 10% to 90%.

i) To obviate the undesired systemic effect of growth factors, the synthetic material is designed to locally release angiogenic factors such as VEGF, HBEGF, bFGF. Additionally, according to an embodiment of the present invention, Bioactive Implants are endowed with a system for the controlled release of angiogenic and antiapoptotic factors.

j) Assessment of the tissue growth and viability. Sensing Electrodes are incorporated in the bioactive implants and connected to a bioelectrical impedance measuring device. The goal of this implantable monitor is to assess by telemetry the evolution of engineered tissue in cardiac regeneration and to detect early pulmonary oedema in heart failure patients.

The invention will be more fully described by reference to the following drawings.

DETAILED DESCRIPTION OF THE INVENTION

Figure 1A:
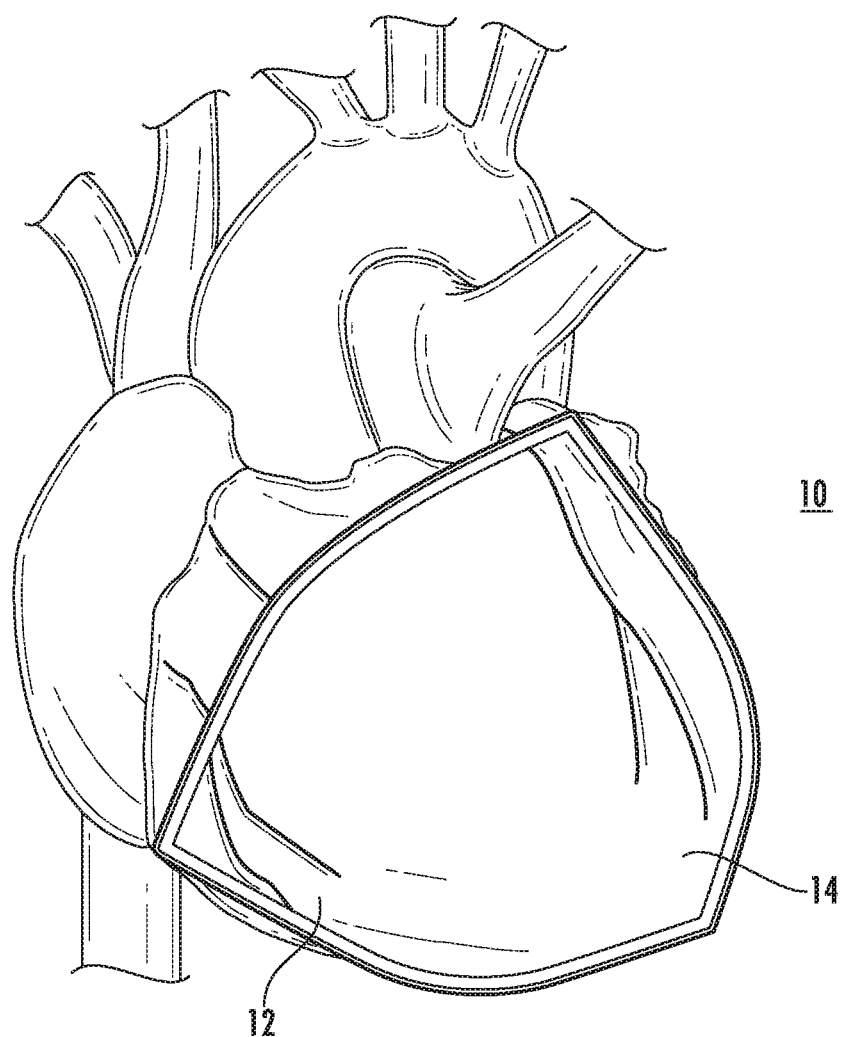
FIG. 1A is a schematic diagram of a bioprosthesis for biventricular heart failure patients.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The present invention provides a bioactive implant for myocardial regeneration and cardiac support.

The bioactive implant of the invention constitutes a scaffold.

As used herein, a scaffold is a material acting as a template for cells to grow and produce new tissue. The scaffold of the invention can be provided in a desired size and shape dependent on the contemplated use. Indeed each ventricle has different wall thickness, wall tension and chamber pressure. To reply to the variety of size and shape, the implant of the invention can notably be provided in the form of a cone or in the form of a square depending on the intended and location use. It can be of a size of from 1 cm$^2$ to 20 cm$^2$. As the bioactive construct of the invention is implanted in the body of a mammal, for example a human, the material of the membrane is chosen to be physiologically inert to avoid rejection or other negative inflammatory response.

According to the present invention, the bioactive implant comprises
  I. an elastomeric microporous membrane (patch) comprising at least:
    a. one non-degradable synthetic polymer and
    b. one partially degradable synthetic polymer
  II. a peptide nanofiber hydrogel and
  III. cells.

As used herein, a membrane is a material having one of its three dimensions (its thickness) much smaller than its other two dimensions (its length and width), these latter being comparable in magnitude. The term patch may be used equivalently instead of the term membrane. An elastomer is a crosslinked macromolecular material which in working conditions is above its glass transition temperature and thus is able to rapidly recover its original unstressed dimensions after cessation of mechanical loading not exceeding a critical value. An elastomeric membrane is a membrane made out of an elastomer. A microporous elastomeric membrane is an elastomeric membrane in which the elastomer configures a system of interconnected void spaces, the pores, throughout the bulk of the membrane, the pores having linear dimensions in the range of several tens to a few hundreds of micrometers. The pores are intended to host cells and the extracellular matrix produced by them. The pores of the microporous elastomeric membrane may also be filled with the peptide nanofiber hydrogel. Alternatively or additionally, the peptide nanofiber hydrogel may be placed on top of the elastomeric membrane. The microporous membrane of the invention configures a three-dimensional environment able to convey mechanical stimuli to the cells and to facilitate three-dimensional cell-to-cell interactions.

According to the present invention, the porosity of the membrane is comprised between 70% and 90%, said pores being interconnected and having preferred diameters comprised between 50 microns and 500 microns, for example between 80 microns and 150 microns.

As used herein, a polymer is a macromolecule consisting in the repeat of a few different units (if one, a homopolymer; if more than one, a copolymer). A synthetic polymer is a polymer not present naturally in biological system. A non-degradable polymer is a polymer which remains chemically unaltered in vivo. The term biostable and the term non-degradable may be used interchangeably. A degradable polymer is a polymer which in vivo undergoes depolymerization (scission) reactions whose products can be toxic or non-toxic, metabolized or non-metabolized by the tissues or organs of the host. The term biodegradable, the term degradable and the term bioresorbable may be used interchangeably. The term biodegradable refers to material that degrade or break down, with time, upon interaction with a physiological environment into components that can be metabolised or excreted by the body. A partially degradable polymer is a polymer composed of at least one non-degradable polymer and at least one degradable polymer.

More specifically, the non-degradable or biostable synthetic polymer a. is selected from the group consisting of polyethylacrylate or polyethylacrylate copolymerized with a 10% wt or a 20% wt hydroxyethylacrylate co-monomer. Scaffolds made of this polymer are advantageously produced by the template leaching method, using as template an arrangement of sintered spheres and/or fiber fabrics. The partially degradable synthetic polymer b. is selected from the group consisting of caprolactone 2-(methacryloyloxy)ethyl ester or caprolactone 2-(methacryloyloxy)ethyl ester copolymerized with ethylacrylate in weight proportions of this last co-monomer comprised between 30% and 80%. Using caprolacton as a component of the partially degradable polymer is particularly advantageous. Indeed since caprolacton is produced by chemical synthesis, it does not produce antigenic reaction, by comparison with collagen.

Also the degradation of a part of the implant reduces a possible risk of chronic restriction of the diastolic function. Indeed, all prosthetic materials implanted around the heart usually produce chronic inflammatory reaction resulting in fibrosis, responsible for the restriction of the diastolic function. The amount of fibrosis is related with the characteristics and the amount of the implanted material. Using a bioactive implant according to the present invention, that is to say an implant containing a biodegradable portion, allows a decrease of the inflammatory reaction with time and thus reduces the possible risk of a restriction of the diastolic function.

Also, it is to be noted that the scaffold membrane of the invention is made of a combination of degradable polymers and partially non-degradable polymers.

The bioactive implant provides a suitable environment for cell homing, growth and differenciation (myocardial repair), as well as mechanical support to the heart. The combination of degradable polymers and partially non-degradable polymers is advantageous because cells implanted in niches will organize, connect and contract more easily with time if they are surrounded by material that degrade with time and if not directly surrounded by a synthetic prosthetic material. However some definitive prosthetic fibres are necessary to avoid progressive heart dilatation. The combination of both polymers, degradable and non-degradable ones, allows a good cells implantation and to keep the scaffold structure.

This polymer is advantageously produced by the template leaching method, using as template an arrangement of sintered spheres and/or fiber fabrics. The percentage of non-degradable polymers versus degradable polymers is comprised between 10 and 90% wt; it is preferably comprised between 10 and 48% wt. The membrane of the present invention is thus a combination of a degradable component and a non-degradable component. Although the membrane comprises at least one polymer that is partially biodegradable, the implant made from such membrane (and thus from such polymer) must maintain the structural integrity for a time required for the intended use.

The membrane of the invention may additionally comprise biomaterials of nanoporous or nanoscale fiber dimensions, for example a coating of hyaluronic acid, independently from the composition and presence of the hydrogel.

As used herein, a hydrogel is a macromolecular material, by which either physical or chemical crosslink interactions produce a macromolecule base component, able to retain large amounts of water molecules. A nanofiber hydrogel is a hydrogel made of nanoporous or nanoscale fibers that percolates above a defined concentration to form a network.

According to an aspect of the invention, the nanofiber hydrogel can be degradable, biologically or chemically, or non-degradable. In certain embodiments, the hydrogel includes natural molecules such as protein, peptide, oligosaccharide, polysaccharide, or proteoglycan derived matrices such as collagens, fibrins, alginates, chitosans, hyaluronic acid, and/or any synthetic molecule that will develop into a nanofiber network with gel/hydrogel properties, such a peptide nanofiber hydrogel scaffold; a class of self-complementary amphiphilic peptides that self-assemble into nanofibers illustrates such peptides. The following peptide AcN-RADARADARADARADA-COONH$_2$ commercially available by the name of PURAMATRIX is an example of this peptide class.

In an aspect of the invention, the nanofiber hydrogel comprises at least one self-assembling peptide (SAPs).

A self-assembling peptide is a peptide with self-complementary properties able to undergo spontaneously a phase transition from a disorder sol state to a more ordered state, where the final ordered state consists of a crystal-like structures or a collapsed amorphous material. The transition is triggered by environmental parameters such as a pH or pK threshold, temperature, etc. A self-assembling peptide gel is the spontaneous assembly of self-complementary peptides developing into ordered chain or domains with elongated shapes and dimensions in the range of a few to tens of nanometers, and are thus referred to as nanofibers. An example of SAP is RAD16-I. Other examples are: RAD16-II (AcN-RARADADARARADADA-COONH$_2$) and KLD12 (AcN-KLDLKLDLKLDL-COONH$_2$.

In a preferred embodiment, the nanoporous or nanoscale fiber hydrogel either completely fills the pores of the elastomer membrane or partially fills the pores by forming a layer coating to the inner surfaces of the membrane's pores.

In a specific aspect of the invention, the membrane is surface-treated to graft adhesion molecules such as functional peptides like as RGD peptides (Arg-Gly-Asp), functional sugars or lipids, and proteins such as laminin or laminin fragments.

The bioactive implant of the invention is designed to feature mechanical properties to be elastic enough to match the myocardium contraction-distraction activity to allow deep structural and functional bio integration.

The implant of the invention has an elastomeric membrane which contains the entire organ to prevent heart dilatation (i.e. a decreased ventricular wall tension).

The bioactive implant, in a particular aspect of the invention, additionally comprises a system for the controlled release or absorbance of active molecules such as any organic molecule, such as small molecule, peptide, lipid, sugar, protein, proteoglycan, with angiogenic, antiangiogenic, pro-regenerative, anti-regenerative, apoptotic, necrotic, antiapoptotic and antinecrotic activity, such as VEGF, IL-6, IL-10, IGF-1, FGF-2, HBEGF, bFGF and chitosan.

Chitosan, a natural polymer of glucosamine and N-acetyl glucodamine, is widely used in the pharmaceutical and tissue engineering fields due to its biocompatibility, biodegradability, and antimicrobial properties. Addition of chitosan improves the physical properties of bioactive implants, and enhances their ability to support endothelial cells and angiogenesis for use in cardiovascular tissue engineering applications.

The release or absorbance system may consist in:

(a) the molecule encapsulated in degradable microparticles made of such polymers as chitosan, hyaluronic acid, complexes of these last two polymers, or a degradable polyester, such as polyglycolic acid, or polylactic acid, or polycaprolactone; the said microparticles embedded in the gel filling or coating the membrane's pores;

(b) the molecule included in the gel filling or coating the membrane's pores associated non-specifically or specifically to the structure of the gel filling material;

(c) the molecule covalently or non-covalently bonded to the self-assembling peptide filling or coating the membrane's pores.

(d) the molecule with absorbance capacity to eliminate any organic molecule with antiangiogenic, anti-regenerative, apoptotic or necrotic activity.

The bioactive implant of the invention, in another aspect, additionally comprises cytokines and angiogenic antiapoptotic peptides.

It has binding capacity of components secreted by the necrotic tissue. Accordingly, it has the ability to modulate and neutralize the effect of components such as Midkine (MDK), a negative regulator of angiogenesis.

The implant of the invention can be functionalized with biological active motifs (peptides and glycopeptides) to promote cellular responses, in particular, myocardial instruction to maintain phenotype, allow cell-cell contact and establishment of gap-junctions.

The bioactive implant of the invention can be designed for elliptical or conical heart shape restoration, in which both ventricles are completely wrapped by the device. The structure of this device consists in special reinforcements at the level of the anatomical bands, forming two helical loops of "non-degradable polymers" for conical shape restoration. The geometric disease in ischemic dilated cardiomyopathy is the spherical chamber, which is different than the elliptical or conical normal heart shape. The use of two helical reinforcement bands allows a three-dimensional recovery of the original ventricular elliptical shape.

The bioactive implant of the present invention comprises cells.

The cells can be myogenic or cardiomyogenic cells. According to this embodiment, the cells are selected from the group consisting of skeletal myoblasts, smooth muscle cells, fetal and neonatal cardiomyocytes, adult ventricular cardiomyocytes, cardiospheres and epicardial progenitors.

The cells can alternatively be angiogenic cells, such as bone marrow and peripheral blood mononuclear fraction, bone marrow and peripheral blood endothelial progenitors, endothelial cells, mesothelial cells from omentum, adipocyte derived stem cells, stem cells from adipose epicardial tissue and multipotent menstrual blood stromal cells.

The cells can also be pluripotent stem cells. In this embodiment, the cells are selected from the group consisting of embryonic cells, animal embryonic cells, adult stem cells, fetal stem cells, neonatal stem cells, non-human stem cells, umbilical cord cells, induced pluripotent stem cells (iPSCs), bone-marrow mesenchymal stem cells (MSCs), adult testis pluripotent stem cells and human amniotic fluid stem cells (hAFSCs). In this regard the bioactive implant is designed to host educated or trained cells expected to grow, multiply, differentiate and organize into a nanoscale fiber within the microporous structure of the patch and to connect with the native myocardium. The combination of the element of the bioactive implant along with the cells is such that it presents a decreased ventricular wall tension and can successfully achieve myocardial regeneration.

According to an aspect of the invention, a mixture of cells is used as component of the bioactive implant. These cells can for example be selected among the following: myogenic cells, cardiomyogenic cells, angiogenic cells and pluripotent stem cells, with the above-given definitions.

Suitable sources of cells for bioactive implant seeding and intrainfarct injection will depend on the types of diseases to be treated. For recent myocardial infarction, angiogenic cells that reduce myocardial necrosis and augments vascular blood flow will be desirable. For chronic heart failure, cells that replace or promote myogenesis, reverse apoptotic mechanisms and reactivate dormant cell processes will be useful. For chronic ischemic cardiomyopathy, both angiogenic and cardiomyogenic cells will be associated.

According to the present invention, it is possible to embed cells in a 3-dimensional structure replicating the extracellular matrix, which is crucial for full tissue restoration and prevention of ventricular remodeling. The clinical translation of cell therapy requires avoidance of potentially harmful drugs and cytokines, and rapid off-the-shelf availability of cells. The combination of pre-differentiated cells within a functionalized scaffold, locally releasing molecules tailored to promote in situ completion of differentiation and improve homing, survival, and functions, circumvents the potential undesired systemic effects of growth factor administration and improve tissue restoration.

The cells seeded into matrix scaffold and supported by a synthetic ventricular support device treated with adhesion molecules ameliorate functional recovery of infarcted hearts and improve long-term evolution by providing myocardial regeneration and gentle support.

The cell-matrix combination associated with a ventricular constraint non-absorbable material such as, mesh cardiac wrap, positioned over the diseased myocardium improves ventricular function and reduces adverse chamber remodelling.

The present invention combines a regenerative biological approach with a prosthetic cardiac support device. Stem cells associated with a tissue engineered matrix scaffold and combined with a mesh cardiac wrap should reduce post-ischemic fibrosis and assist the recovery of myocardial viability and compliance. This procedure can be proposed for the treatment of ischemic heart disease, associating a regenerative biological approach with a prosthetic support device.

The present invention constitutes a unique platform for engineering highly efficient contractile tissues and enhancing cell therapy.

For the present invention, the cells can be obtained from any suitable source. They can be purchased or they can be isolated from a suitable source by methods well known to those skilled in the art. They may be cultured according to methods known to those skilled in the art. For example, the cells can be added to culture medium which may additionally comprise growth factors, serum, antibiotics or any of a variety of cell culture components known to those skilled in the art.

Ischemic cardiomyopathy induces geometric alteration of the ventricular cavity, which changes from an elliptical to a spherical shape. The geometric disease in ischemic dilated cardiomyopathy is the spherical chamber, which is different than the elliptical or conical normal heart shape. The sphericity index quantifies this geometric form alteration by comparing the transverse ventricular (short) and long axis; an ellipse has a 0.5 ratio (the length is twice the width) and a sphere is 1.0 due to similar transverse and longitudinal dimensions.

According to one embodiment of the invention, the structure of the bioactive implant of the present invention consists in special reinforcements at the level of the anatomical bands, forming two helical loops of non-degradable biostable synthetic polymers. This embodiment of the present invention is intended to cover both ventricles for ischemic dilated cardiomyopathy. Helical ventricular artificial bands for LV elliptical shape restoration using bioactive implants is useful in the context of the biosurgical strategies indicated to manage patients with advanced myocardial diseases. An important advantage of this technique is the fact that the surgery is performed without the risk of opening the ventricular chambers, i.e. without extracorporeal circulation.

In another aspect, the present invention deals with a method for preparing the bioactive implant of the invention, comprising the steps of filling an elastomeric microporous membrane with a nanofiber hydrogel, so as to obtain a bioactive construct. In this respect, the filling is for example made by placing a syringe into the membrane, said syringe being filled with the gel and gently evacuating the air in the pores; according to another step, said construct is cultured under biophysical, mechanical conditions (i.e. compression and elongation); then a step of seeding or implanting cells onto or into said bioactive construct using the following methods: mechanical (shaking, centrifugation), chemical (electrophoresis), physical (electroporation). The cells that can be used are myogenic, cardiomyogenic, angiogenic or pluripotent stem cells.

Another method for preparing the bioactive implant of the invention comprises the steps of obtaining cells, for example, myogenic, cardiomyogenic, angiogenic or pluripotent stem; culturing said cells in vitro; mixing said cells with a nanofiber hydrogel; and filling an elastomeric microporous membrane with said cell-containing nanofiber hydrogel, so as to obtain a bioactive construct. The method of the invention may also comprise the step of culture of said bioactive construct under local in vitro electrostimulation.

In a specific aspect of the method, the cells are cultured under lowered oxygen tension.

In a still specific aspect of said method, the bioactive implant is cultured so as to be adapted to left ventricular and/or right ventricular support and regeneration, for partial or complete ventricular wrappings.

The present invention also deals with a method for repairing the myocardium of an individual comprising the steps of preparing a bioactive implant according to the invention and implanting the bioactive implant into and/or onto the myocardium.

In a more specific aspect, the method for repairing the myocardium comprises an additional step consisting in injecting cells through the epicardium during cardio-thoracic surgery, thoracoscopy or computer-robotic assisted procedures. The injected cells can be autologous stem cells cultured in hypoxic conditions.

The present invention also deals with an elastomeric microporous membrane, comprising at least one non-degradable polymer, at least one partially degradable polymer, and at least one biomaterial of nanoporous or nanoscale fiber dimensions, said membrane having a porosity comprised between 70% and 90%, the pores being interconnected and having diameters comprised between 50 microns and 500 microns, for example between 80 microns and 300 microns, preferably between 80 microns and 150 microns, wherein a. the non-degradable polymer is selected from the group consisting of poly(ethylenglycol diacrylate), polyethylacrylate and polyethylacrylate copolymerized with a 10% wt or a 20% wt hydroxyethylacrylate comonomer; and b. the partially degradable polymer is selected from the group consisting of polycaprolactone, caprolactone 2-(methacryloyloxy)ethyl ester and caprolactone 2-(methacryloyloxy)ethyl ester copolymerized with ethylacrylate in weight proportions of this last comonomer comprised between 30% and 80%, wherein the percentage of non-degradable polymers versus degradable polymers is comprised between 10% wt and 90% wt.

This membrane may be used in a bioactive implant for myocardial regeneration and ventricular chamber support.

In a more specific aspect, the elastomeric microporous membrane can be surface-treated to graft adhesion molecules. The adhesion molecules being selected from the group consisting of functional peptides such as RGD peptides, functional sugars or lipids, and proteins such as laminin or laminin fragments.

The present invention also deals with a method for surgical myocardial repair, comprising the steps of:

a) mixing cells with a nanofiber hydrogel, b) positioning the elastomeric microporous membrane of the invention at the intended location of the body, and c) injecting or spreading the mix obtained in step a) into or onto the positioned elastomeric microporous membrane.

The present invention also concerns a method for surgical myocardial repair, comprising the steps of:

a) mixing cells with a nanofiber hydrogel, b) injecting or spreading the mix obtained in step a) into or onto the elastomeric microporous membrane of the invention, so as to obtain a bioactive implant, and c) positioning the bioactive implant of step b) at the intended location of the body.

Figure 1B:
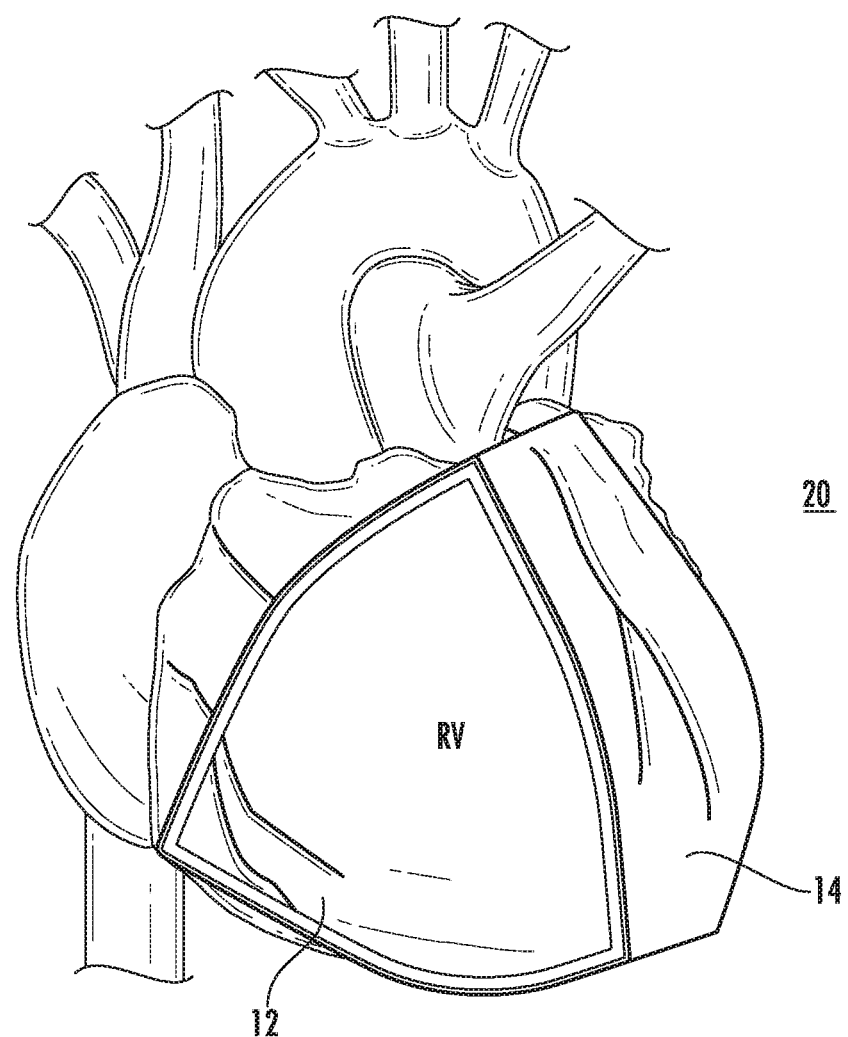
FIG. 1B is a schematic diagram of a bioprosthesis for right ventricular heart failure patients.
Figure 1C:
FIG. 1C is a schematic diagram of a bioprosthesis for left ventricular heart failure patients.

FIG. 1A-1C illustrate adapted ventricular wrapping. FIGS. 1A-1C show devices for complete ventricular wrapping. FIG. 1A is used for biventricular heart failure patients. Bioprosthesis 10 is made of the same material for both right ventricle 12 and left ventricles 14. Bioprosthesis 10 can be formed of the elastomeric microporous membrane. FIG. 1B is used for right ventricular failure patients. Bioprosthesis 20 is made of high rate [60 to 80%] of biodegradable material in left heart side 14 and the elastomeric microporous membrane on the right heart side 12. FIG. 1C is used for left ventricular failure patients. Bioprosthesis 30 is made of high rate of biodegradable material in right heart side 12 and the elastomeric microporous membrane on the left heart side 14.

Bioprosthesis 10, 20, 30 can be reinforced by helical loops made of non-degradable or semidegradable polymers. These materials can be the following: polyethylacrylate (PEA) copolymerized with hydroxyethylacrylate comonomer, semi degradable methacrylate-endcapped caprolactone (CLMA), polyethylene terephthalate (PET), polypropylene, polydioxanone, polyglecaprone, e-caprolactone, poly-L-lactide polymers, poly salicylic acid polymer, poly desaminotyrosyl-trypsine ethyl ester polymer, polycarbonate urethane, polyurethanes, poly(glycerol sebacate) (PGS), elastin, silk.

Loops are made of a band of 30 mm to 40 mm width with 1 mm to 2 mm uniform thickness, or made with thickness progressively increased from 1 mm to 3 mm.

Helical loops follow the anatomical heart configuration, where muscular ventricular bands begin at the insertion of the pulmonary artery in the right ventricle and ending at the aortic valve annulus (LV). The role of myocardial band is to limit ventricular dilatation, preserving elliptical shape, and contribute to systolic contraction and diastolic filling (suction mechanism).

In one approach, a helical loop can be integrated into the ventricular bioprosthesis structure during manufacturing.

In another approach, a helical loop is a complement of a bioactive patch fixed onto a myocardial pathologic zone, during surgery or thorascocopic approach.

In another approach, a helical loop is fixed around the heart as a complement of the ventricular support bioprosthesis, implanted to cover the ventricles during surgery or thorascocopic approach.

In another approach, a helical loop can be used as a single therapeutic procedure.

Figure 2A:
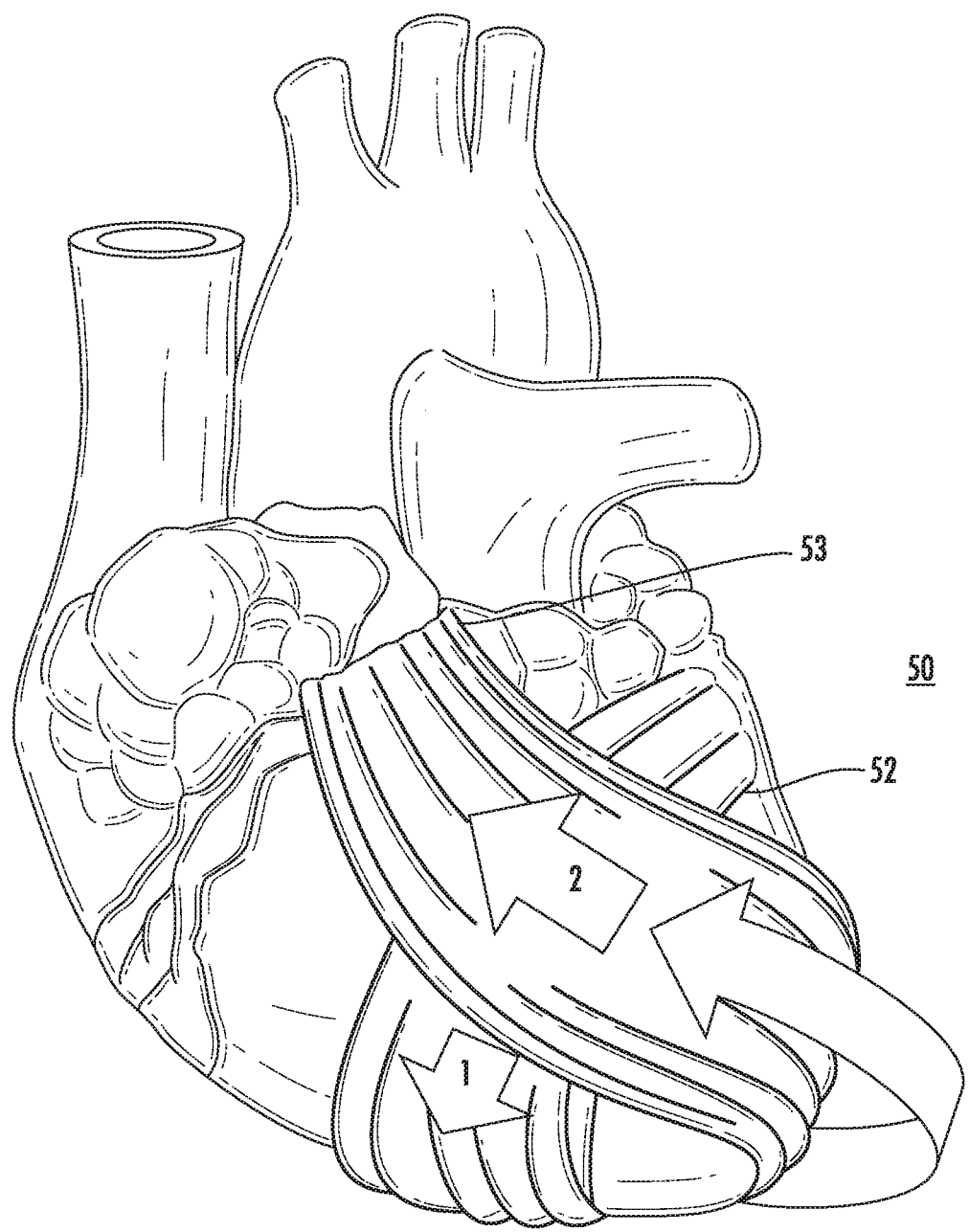
FIGS. 2A and 2B are schematic diagrams of a single helical loop used to reinforce the bioprosthesis.
Figure 2B:
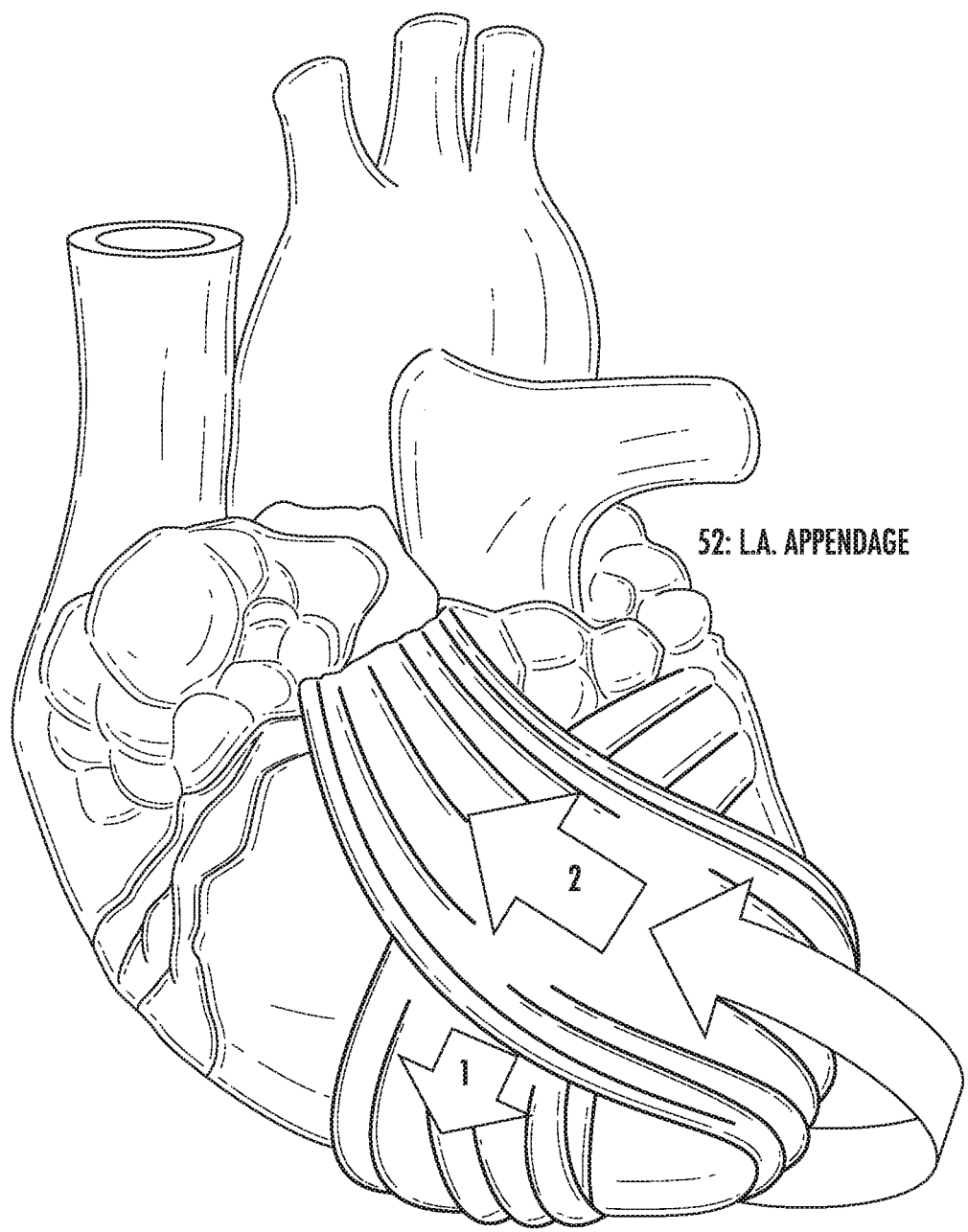

For moderate heart dilatation, single apical loop 50 is used to wrap ventricles, starting at the level of the left atrial appendage 52 and ending at the aortic root 53, as shown in FIG. 2. (See FIG. 2B showing the position of the left atrial appendage 52).

Figure 3:
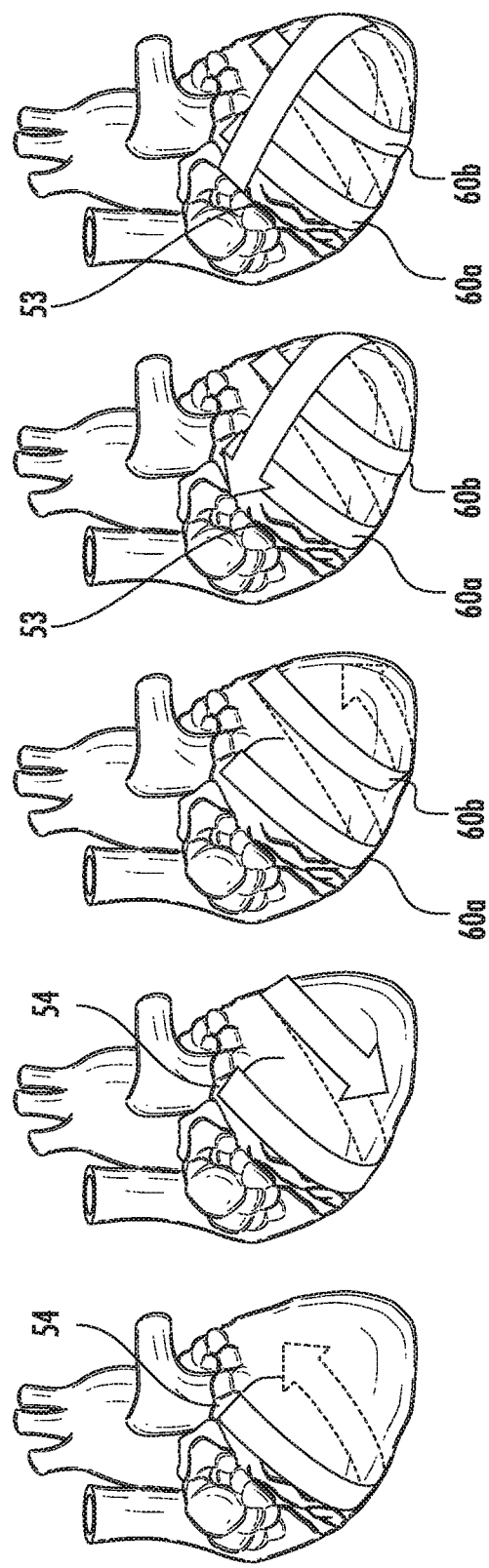
FIG. 3 is a schematic diagram a double loop used to reinforce the bioprosthesis.

For severe heart dilatation, double basal and apical ventricular helical loops 60a, 60b are used, starting at the level of pulmonary artery root 54 and ending at the level of the aortic root 53, as shown in FIG. 3. Fixation of the loop/band onto the heart, onto the bioactive patch and onto the ventricular support bioprosthesis can be made by surgical sutures and/or surgical clips and/or glue of biological or synthetic origin.

The method for implantation of small bioactive patches or large cardiac support bioprostheses can be performed during cardio-thoracic surgery, thoracoscopy or computer-robotic assisted procedures. After gaining access, the pericardium is open to expose the heart.

Figure 4A:
FIGS. 4A and 4B are schematic diagrams of a bioactive patch.
Figure 4B:
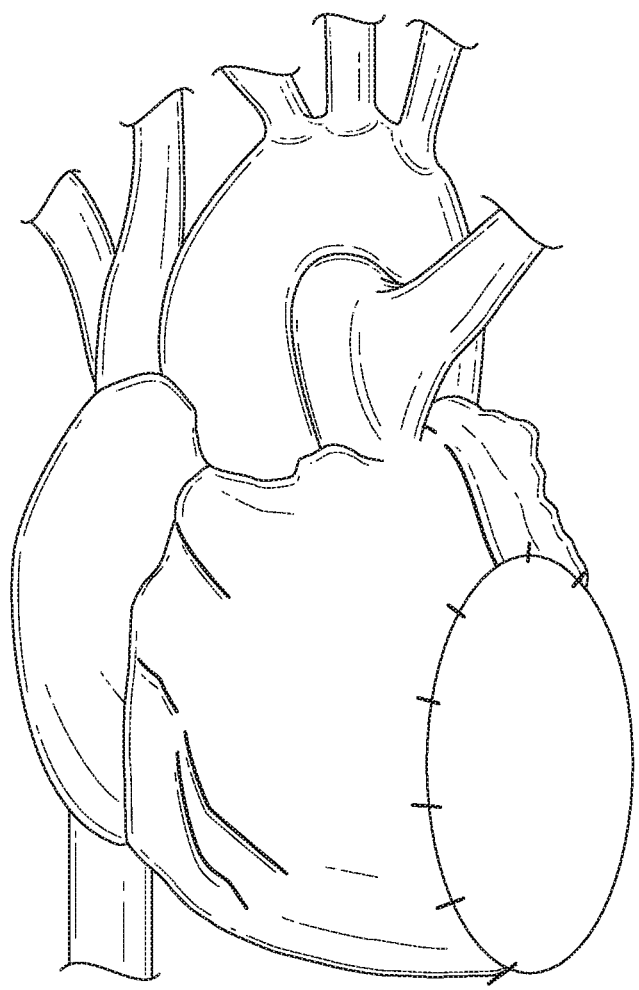

In a bioactive patch implantation procedure, scaffold 70 is positioned onto the pathologic myocardial lesion, for example covering the infarct and pen-infarct zones. It is fixed to the epicardium by single interrupted sutures 72 (4-0 or 5-0) and covered by the pericardium, as shown in FIGS. 4A and 4B.

Figure 5:
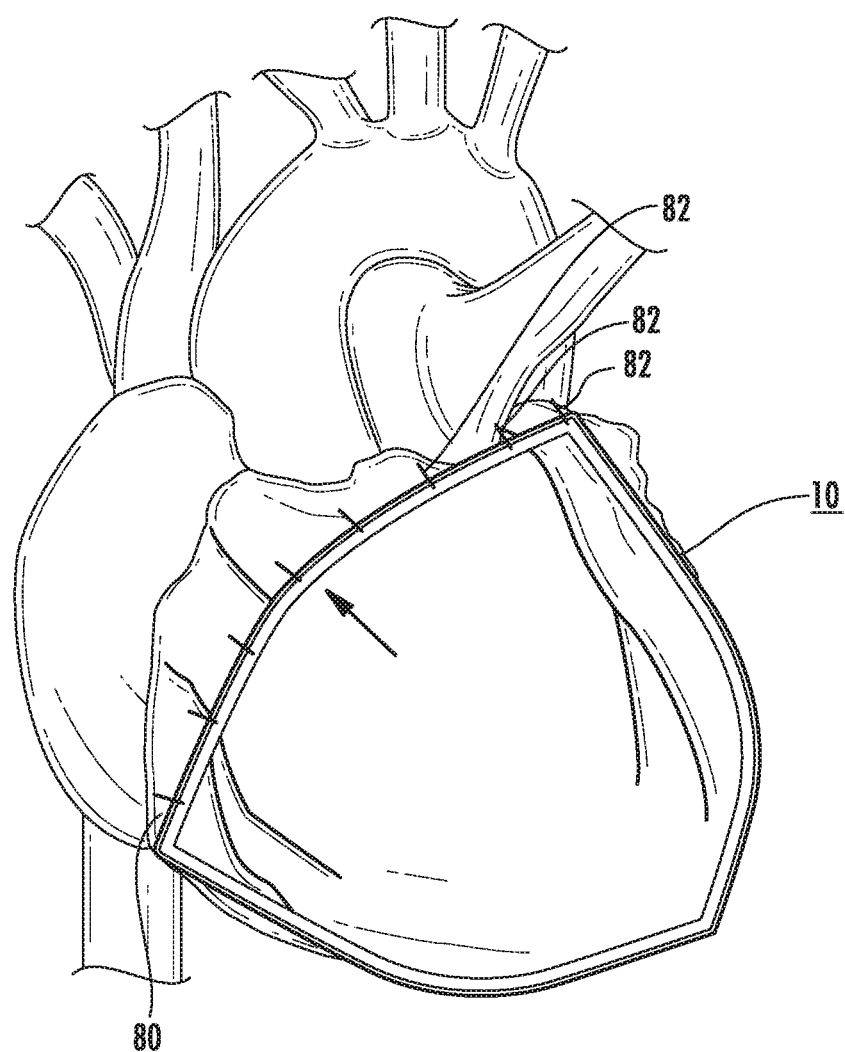
FIG. 5 of the bioprosthesis fixed with epicardial interrupted sutures.

In ventricular support biprothesis implantation procedure, for a device choice, the size of the heart is measured by a circumferential tape. Adequate size of biprothesis 10, 20, 30 is chosen and placed around right ventricle 12 and left ventricle 14, as shown in FIG. 5. Bioprosthesis is placed around the ventricles by sliding it gently into position (arrow), from the apex of the heart to the atrio-ventricular groove Bioprothesis 10, 20, 30 is fixed with epicardial interrupted sutures 82 (4-0) to heart 80 at the level of the A-V groove, starting at the most posterior location. For example, fixation sutures are placed every 2 cm to 3 cm.

The sequential contraction of the ventricular myocardium results in the successive shortening and lengthening of the ventricles. These movements may determine the ejection and suction of blood, respectively. The shape and duration of ventricular filling/emptying mechanism can be compared to a stroke action induced by a piston water pump. Surgical interventions for heart failure like reduction ventriculectomy have not proven surgically efficacious. Removal of apical or basal ventricular segments and the muscle bands seems to interfere with the natural sequence of myocardial contraction and diastolic filling. Cardiac wrapping by ventricular support bioprostheses of the present invention, having bands spatially distributed as helicoids, is an advantageous physiological therapeutic method.

EXAMPLES

Example 1: Biological Evaluation of Elastomeric Scaffold Membranes

Quantification of Cell Proliferation.
MTT Assay

The MTT system is a simple, accurate, reproducible means of measuring the activity of living cells via mitochondrial dehydrogenase activity. The key component is 3-[4,5-dimethylthiazol-2-yl]-2,5-diphenyl tetrazolium bromide or MTT. Solutions of MTT solubilised in tissue culture media or balanced salt solutions, without phenol red, are yellowish in color. Mitochondrial dehydrogenases of viable cells cleave the tetrazolium ring, yielding purple MTT formazan crystals which are insoluble in aqueous solutions. The crystals can be dissolved in acidified isopropanol. The resulting purple solution is spectrophotometrically measured. An increase in cell number results in an increase in the amount of MTT formazan formed and an increase in absorbance.

Material and Method

Pieces of elastomeric microporous membranes of polyethyl acrylate (PEA100 in what follows) and a copolymer of ethyl acrylate and hydroxyethyl acrylate with a 90:10 mass ratio of both monomers (hereafter PEA90) were employed. The membranes had been cut into pieces of dimensions 25 mm×25 mm, with an approximate thickness of 1.0 mm (PEA100 and PEA90A) and of 0.7 mm (PEA90B). The porosity of the membrane was 70%. The pores of the membranes consisted in layers of orthogonal families of parallel cylindrical pores, with pore diameter of 150 microns and pore separation of 300 microns. They were generated by letting the precursors of the polymers react inside a mould with a template of layers of porogen orthogonal fibers, and dissolving the template afterwards to give place to said pores.

Scaffolds Conditioning Protocol

Due both to their hydrophobic nature and to their microporous structure, the elastomeric membrane needs to be pre-hydrated before cell seeding. The conditioning procedure consists in a 24 h immersion in a PBS solution. Vacuum might be necessary to improve fluid penetration into the pores, putting the sample in a tube sealed hermetically with a cap pierced by a syringe's needle, and performing vacuum with the syringe. The pre-hydrated sample is then immersed in the culture medium. If the pH changes, the medium is renewed until the reference pH value remains stable.

Cell Seeding

Bone marrow mesenchymal stem cells (BMC) were isolated under sterile conditions from femur and tibia bones of Wistar rats. After 2 weeks of in vitro cultures in DMEM complete medium with L glutamine, sodium pyruvate and 15% Fetal Bovine Serum (1$^{st}$ passage), 10,000 cells diluted in 0.5 ml medium were seeded into PEA90 and PEA100 scaffolds and into 3D Collagen type I matrix (n=5 for each sample). After careful cell seeding using a micropipette, elastomeric scaffolds and collagen matrix were maintained 20 minutes without motion, to start cell adhesion. At the following step, and in order to promote a regular distribution of BMC into the matrix pores, Petri dishes containing the elastomeric and collagen scaffolds/matrices were shaken continuously for 10 minutes at 80 g using an Orbital Shaker (Stuart Scientific, Stone, Staffordshire, UK). Afterwards cell seeded scaffolds were incubated one hour at 37° C. Finally DMEM complete medium was added to the Petri dish and the cell seeded scaffolds/matrix were cultured during 3 weeks at 37° C., 5% $CO_2$.

Quantification of Cell Propagation

Cultures were removed from the incubator into a laminar flow hood. The supernatant was removed and then the scaffolds were washed with PBS two times. The scaffolds were transferred into new tubes (15 ml Falcon). Aseptically the MTT solution was added in an amount equal to 10% of the culture volume (1800 microliter phenol red free medium+180 microliter MTT) and cultures were incubated for 3 hours at 37° C. in a 5% CO2 humidified atmosphere. Two ml of solubilisation solution or solvent were added and then vortexed for 5 min. This provoked the release from the scaffold of MTT which was actively reduced by viable cells acquiring a yellow colouring. Each sample was centrifuged at 15,000 g for 5 min and the supernatant was read at 570 nm using a multiwell spectrophotometer.

Results

Spectrophotometer assessments showed optical density (OD) values of 0.13+/−0.02 for collagen matrix; 0.22+/−0.04 for PEA90A scaffolds; 0.11+/−0.03 for PEA90B scaffolds; and 0.34+/−0.05 for PEA100 scaffolds.

These results showed that cell proliferation was well developed in the elastomeric scaffolds, presenting a better proliferation than the 3D collagen scaffolds. Until now collagen scaffolds have been used in experimental and clinical myocardial tissue engineering as a gold standard.

Example 2: Electrophysiological Evaluation of the Elastomeric Scaffold Membranes Measurements of Electrical Impedance Electrical Conduction Myocardial electrical impedance has shown to be an effective indicator of myocardial tissue characteristics and electrode tissue interface. Significant modifications have been demonstrated during tissue ischemia.

Electrical resistivity (also known as specific electrical resistance or volume resistivity) is a measure of how strongly a material opposes the flow of electric current. A low resistivity indicates a material that readily allows the movement of electrical charge. The SI unit of electrical resistivity is the ohm [$\Omega$].

Material and Methods

Pieces of microporous membranes of polyethyl acrylate (PEA100 in what follows) and a copolymer of ethyl acrylate and hydroxyethyl acrylate with a 90:10 mass ratio of both monomers (hereafter PEA90) were employed. The membranes had been cut into pieces of dimensions 25 mm×25 mm, with an approximate thickness of 1.0 mm (PEA100 and PEA90A) and of 0.7 mm (PEA90B). The pores of the membranes consisted in layers of orthogonal families of parallel cylindrical pores, with pore diameter of 150 microns and pore separation of 300 microns. They were generated by letting the precursors of the polymers react inside a template of the porous structure, and dissolving the template afterwards.

Scaffolds Pre-Hydration

Elastomeric scaffolds need 2 days of pre-hydration as follows: 24 Hs immersion in a PBS solution and 24 Hs immersion in culture medium. Vacuum could be necessary to improve tissue hydration, putting the sample in tube with cap and performing vacuum with a syringe. Once pH change is observed, the samples should be overnight in fresh culture medium.

Electrophysiological Studies

Two electrodes having curved needles for easy insertion were sutured into the opposites borders of the elastomeric scaffolds and of 3D collagen type I matrix (n=5 for each sample). These electrodes were conceived to be implanted for temporary postoperative cardiac pacing in heart surgery. Scaffolds and implanted electrodes were immersed in Petri dishes containing DMEM cell culture medium. After 30 minutes electrophysiological studies were performed connecting the electrodes to a Pacing System Analyzer Model 5311 (Medtronic Inc.). Bipolar charge balanced electro-stimulation was delivered using the following parameters: pulse amplitude 1 Volt, pulse width 0.5 ms, frequency of stimulation 70 pulses per minute (ppm). Electrostimulation was delivered just for testing. Afterwards electrical impedance within the scaffolds was assessed.

Results

Electrical measurements were performed in each preparation group, i.e. cell medium alone, collagen matrix, PEA90A scaffold, PEA90B scaffolds, PEA100 scaffolds. Each group consisted of 5 samples.

Impedance measurements showed the following values: cell culture medium 292+/−25 ohms, collagen matrix 230+/−21 ohms; PEA90A scaffolds 321+/−34 Ohms; PEA90B scaffolds 345+/−33 ohms; PEA100 scaffolds 340+/−29 ohms.

|  | Cell medium | Collagen matrix | PEA90A scaffold | PEA90B scaffold | PEA100 scaffold |
| --- | --- | --- | --- | --- | --- |
| Impedance [$\Omega$] | 292 | 230 | 321 | 345 | 340 |
| Current [mA] | 3.42 | 4.35 | 3.11 | 2.90 | 2.94 |

Pacing pulse; 1.0 V, 0.5 ms

These results showed that all the evaluated materials present electrical conduction properties, i.e. resistance, similar to those encountered with cardiac tissues, thus these scaffolds have the potential to be used for myocardial substitution.

Example 3

The failing cardiac muscle needs to be chronically supported to decrease ventricular wall stress and also to be regenerated to improve ventricular function. This Example demonstrates that the association of stem cells with a collagen matrix and a polyester mesh for cardiac wrap provides better results than the implantation of polyester mesh alone.

To illustrate this embodiment, fifteen sheep underwent 1 hour of surgical myocardial ischemia followed by reperfusion. Three groups were created: Group 1: coronary occlusion without treatment (control group). Group 2: LV constraint using a polyester mesh for cardiac wrap. Group 3: the ischemic area was treated associating stem cells, a collagen matrix and a polyester mesh. Autologous adipose tissue derived stem cells (ASC) cultured in hypoxic conditions (5%) were labelled with BrdU and injected into the infarct area and into a collagen matrix. At 3 months animals were evaluated with echocardiography and histopathological studies.

Biopsy Extraction

In 15 female Rambouillet sheep weighing 32 to 37 kg (mean 35±2.2 Kg), subcutaneous fat tissue was removed for stem cell isolation and expansion. Autologous cells were used throughout in order to avoid any problem of histocompatibility. Adipose tissue biopsies were obtained by subcutaneous fat tissue removal (40-60 grams) from the right thoracic wall and stored in phosphate buffered saline (PBS) at room temperature until processing.

Isolation and Hypoxic Culture of Adipose Derived Stem Cells (ASC)

The tissue samples were finely minced and digested by incubation in a 0.14 Wünsch units/mL Liberase Blendzyme 2 (Roche Applied Science, Hvidovre, Denmark) solution at 37° C. for two hours. The digests were centrifuged at 400 g for 10 min and the top fluid and fat layers were discarded. Contaminating erythrocytes were lyzed by resuspension of the pellet in sterile milli-Q water for 20 seconds, after which the salt concentration was adjusted through addition of 10×PBS. The cells were filtered through a 100 μm cell strainer, centrifuged at 400 g for 10 min, and resuspended in 25 mL growth medium, consisting of minimum essential medium alpha (A-MEM) (GIBCO/Invitrogen) supplemented with 10% fetal bovine serum (FBS), and penicillin (10 U/ml), streptomycin (10 mg/ml), gentamicin (10 mg/ml) (all from GIBCO/Invitrogen). The cells were seeded in a T75 flask and transferred to a $CO_2$ incubator overnight, after which non-adherent cells were removed. The flasks were then transferred to a hypoxic workbench/incubator (Xvivo; Biospherix, Lacona, N.Y.), allowing for uninterrupted cell culture and passaging in a controlled atmosphere of 5% $O_2$ and 5% $CO_2$ balanced with nitrogen. During expansion of the cells, the media was changed twice a week. When cells were 90% confluent, the cells were detached from the culture flasks using 0.125% trypsin/0.01% EDTA and transferred to new flasks.

Labeling with Bromodeoxyuridine

For each sample, the cells were expanded until eight T175 culture flasks were 75% confluent, then the cells were labeled with bromodeoxyuridine (BrdU). Briefly, cells were incubated with growth media containing 10 micrograms BrdU (Sigma) for 48 hours, and then the cells were washed several times with PBS and frozen in aliquots of approximately $10 \times 10^6$ cells.

Experimental Myocardial Injury

After preoperative medication and induction of anaesthesia (same protocol as fat tissue biopsies) animals were intubated and mechanically ventilated with an Aestiva/5 system (Datex-Ohmeda, Helsinki, Finland). The electrocardiogram was monitored during operation. A central venous line was placed through the external jugular vein for administration of fluid and drug infusions. Left thoracotomy was performed at the level of the 5th intercostal space, and the heart was exposed. To reduce the risk of ventricular fibrillation, a continuous IV perfusion (2 mg/kg per hour) of Xylocaine 1% (Lidocaine, AstraZeneca) was performed during the entire surgical procedure. In all animals a LV myocardial ischemia was surgically created by transitory ligation (60 minutes) of the main diagonal branch of the left coronary artery, followed by reperfusion. A 4-0 non-absorbable Prolene suture was passed underneath the coronary artery branch, the flow was interrupted using a Teflon pledget compressed by a polyurethane occluder. This occluder was released after 60 minutes, thus the myocardial ischemic territory was reperfused. Significant EKG changes, including widening of the QRS complex and elevation of the ST segment, and colour and kinetics changes of the area at risk were considered indicative of coronary occlusion.

Treatment Groups

Animals were randomized in 3 groups:

Group 1 (n=5): myocardial ischemia without treatment (control group).

Group 2 (n=5): post-ischemia implantation of a mesh ventricular wrap device.

Group 3 (n=5): post-ischemia intrainfarct injection of stem cells, implantation of a collagen matrix as interface and implantation of the mesh ventricular wrap device.

Cell Injection and Collagen Matrix Implantation

In Group 3 animals, at 1 hour of infarction cell were injected into the infarct zone by using a 27-gauge needle. Injections consisted of 99+/−12 million cells, 50% (2 mL) injected into the infarction and 50% (5 mL) seeded into a 3D collagen type I matrix.

For myocardial treatment, six injection needle points were used in each animal, bulging over the myocardial infarction area was confirmed in every case after injection. Criteria to guide the epicardial injections were the ventricular surface discoloration and hypokinesia.

Collagen Matrix Preparation

Collagen matrix was prepared from a commercially available CE Mark collagen kit (Pangen 2, Urgo Laboratory, Chenove, France). This 3D biodegradable matrix (size: 5×7×0.6 cm) was manufactured using a lyophilised, non denatured, native type I collagen. The matrix pores measured 50 to 100 μm. In the operating room and under high sterility conditions, matrix was placed into a Petri dish; afterward, the cell suspension (50±6 million cells diluted in 5 mL medium) was seeded onto the matrix. To promote a regular distribution of ASC into the matrix pores, Petri dishes containing the collagen matrix was shaken continuously for 10 minutes at 160 g using an Orbital Shaker (Stuart Scientific, Stone, Staffordshire, UK).

Mesh Cardiac Wrap

To avoid hemodynamic instability and arrhythmias during implantation, we start to fix the mesh cardiac wrap (CorCap polyester device) before creation of myocardial ischemia. The CorCap model Gen2 CSD Size B (Acorn Cardiovascular Inc, St Paul, Minn., USA) was chosen in all cases, then was opened longitudinally, slid behind the ventricles and fixed with 2 lateral epicardial sutures (Prolene 4-0). Afterwards the ischemia was created followed by reperfusion. One hour later the cells were injected, the collagen matrix implanted and the anterior part of the CorCap was closed using a continuous suture (Prolene 2-0). The fixation of the device was completed by multiple single sutures over the atrio-ventricular anterior groove.

Results

No mortality was observed. The hypoxic treatment for cell cultures demonstrated a quite dramatic improvement of proliferation rate: under hypoxia cells grown faster. Echocardiography showed a limitation of LVED (Left Ventricular End-diastolic Dimension) volume in both treated groups (polyester mesh alone 35.6±5 mL and with cell therapy 32.6±4 mL) vs. control (65±6.3 mL, p<0.01 for both comparisons). EF (Ejection Fraction) was significantly greater in the hearts treated with the polyester mesh+cells/ collagen (55.8±3.8%) compared with those receiving polyester wrapping-only (44.1±2.3%) (p=0.04) or without treatment (34.8±3.6%) (p=0.01). Doppler-derived mitral valve deceleration time (DT) improved from 140±6.3 ms to 195±9.5 ms (p=0.03) in the cell-collagen CorCap group but not in the other groups. Histology showed in the cell treated group multifocal ischemic areas much less prominent than in other groups, with focuses of angiogenesis and viable grafted cells. Minimal fibrosis interface between the polyester mesh and the epicardium was observed in Group 3, probably due to the interposition of the cell-seeded collagen.

Comments

In an ischemic model, stem cells associated with a collagen matrix and a polyester mesh for cardiac wrapping improves EF and diastolic function, reducing adverse remodelling and fibrosis. This procedure associating a regenerative biological approach with a prosthetic support device seems to be appropriate for the treatment of advanced ischemic heart failure.

Example 4

This clinical Example demonstrates that a cell-seeded collagen matrix associated with intra-infarct cell therapy provides better results than stem cell alone.

Matrix Preparation

A 3D biodegradable matrix (size: 5×7×0.7 cm) manufactured using lyophilized bovine type I collagen was prepared. The matrix pores measured 50 to 100 μm. In the operating room and under high sterility conditions, matrix was placed into a Petri dish; afterward, the cell suspension (250±28 million cells diluted in 10 ml medium) was seeded onto and into the matrix. To promote a regular distribution of cells into the matrix, Petri dishes containing the matrix were shaken continuously for 10 minutes at 160 g using an Orbital Shaker (Stuart Scientific, Stone, Staffordshire, UK).

Surgical Procedure

In 10 patients (mean age 52.6 y), after sternotomy, a single OP-CABG (off pump-coronary artery bypass graft) was performed using the left internal mammary artery (LIMA). At the end of surgery, 250±28 million cells diluted in 5 ml medium were injected in the infarcted area and borderzone, using a 25G×40 mm retrobulbar ophthalmic needle. Then the cell seeded matrix was placed covering the infarcted area and fixed to the epicardium with 6 PDS sutures (6-0).

In another group of 10 patients (mean age 56.8 y), a single OP-CABG was performed. Stem cells were injected into the infarction scar but no seeded matrix was used in this group.

Results

There was no mortality and any related adverse events (follow-up 10-3.5 months). NYHA FC improved in both groups from 2.3±0.5 to 1.3±0.5 (matrix, p=0.0002) vs 2.4±0.5 to 1.5±0.5 (no matrix, p=0.001). LV end-diastolic volume evolved from 142.4±24.5 to 112.9±27.3 mL (matrix, p=0.02) vs 138.9±36.1 to 148.7±41 mL (no matrix, p=0.57), LV filling deceleration time improved significantly in the matrix group from 162±7 ms to 198±9 ms (p=0.01) vs no-matrix group (from 159±5 ms to 167±8 ms, p=0.07). Scar area thickness progress from 6-1.4 to 9-1.1 mm (matrix, p=0.005) vs 5-1.5 to 6-0.8 mm (no matrix, p=0.09). EF improved in both groups, from 25.3-7.3 to 32-5.4% (matrix, p=0.03) versus 27.2-6.9 to 34.6-7.3% (no matrix, p=0.031).

Comments

This clinical study showed that cell transplantation associated with a collagen cell-seeded matrix increased the thickness of the infarct scar with viable tissues and help to normalize cardiac wall stress in injured regions (scaffold effect), thus limiting ventricular remodelling and improving diastolic function. Patients treated without the cell-seeded collagen matrix didn't show limitation of post ischemic remodelling and improvements in diastolic function.

Example 5

Preparation of an Hybrid Material for Three-Dimensional Culture with Improved Mechanical Properties Filling Elastomeric Membranes with Self-Assembling Synthetic Peptides Resuspended in Water Mechanical Properties of Three Dimensional Scaffolds During the last decades cellular cardiomyoplasty has become a state of art for cardiac affects. It consists in introducing myocardial or stem cells (with and without three-dimensional matrices) in the infarcted ventricles trying to recover the lost function. The drawback is that it was proved that there were a low number of cells capable of surviving in these conditions; partly because they cannot stand the mechanical forces of the receptor tissue.

Three-dimensional scaffolds as RAD16-I (self-assembling peptides resuspended in water) allow the cells to form a functional network in the (β-sheet scaffold formed, but additionally it is indispensable that the scaffold could stand the beat of the heart. Elastomeric membranes can offer these mechanical properties.

Congo Red Staining

Congo red staining is a simple method to appreciate the formation of typical RAD16-I self-assembly (β-sheet. The reactive is as sodium salt of benzidinediazo-bis-1-naphthylamine-4-sulfonic acid (formula: $C_{32}H_{22}N_6Na_2O_6S_2$) and its configuration permits hydrogen bonding of the azo and amine groups of the dye to similarly spaced hydroxyl radicals giving a red coloration.

Materials and Methods

Pieces of microporous membranes of polyethyl acrylate (PEA100 in what follows) and a copolymer of ethyl acrylate and hydroxyethyl acrylate with a 90:10 mass ratio of both monomers (hereafter PEA90) were employed as elastomeric membranes. The membranes had been cut into pieces of dimensions 0.5 cm×0.5 cm, with an approximate thickness of 1.0 mm (PEA100 and PEA90). The pores of the membranes consisted in layers of orthogonal families of parallel cylindrical pores, with pore diameter of 150 microns and pore separation of 300 microns. They were generated by letting the precursors of the polymers react inside a template of the porous structure, and dissolving the template afterwards.

The self assembling peptide RAD16-I was used as three-dimensional scaffold. The stock was prepared in 1% solution of sucrose 10% avoiding the self-assembling produced by the increase of the ionic strength. The stock solution is diluted to the desired concentration in sucrose 10% for each experiment.

Scaffolds Pre-Hydration

The elastomeric scaffolds needed to be pre-conditioned before the peptide addition. Initially the membranes were sterilized using three washes with EtOH 70% and letting them dry in air during 10 min. After this pre-treatment the scaffolds were hydrated as follows: 30 min of immersion in a PBS solution with vacuum and three washes with sucrose 10%. The vacuum was necessary to ensure that all the pores were filled with the aqueous solution, and the isotonic solution was necessary to avoid the self-assembly during the first contact between the membranes and the peptide. After this treatment, the membranes were dried to moist since the complete drying would return the membranes to their initial hydrophobicity.

Filling of the Membranes with RAD16-I Peptide

The pre-treated membranes were introduced inside a 9-mm-diameter cell culture insert (PICM01250, Millipore, Billerica, Mass.). Then RAD16-I peptide 0.15% in sucrose 10% was loaded, carefully, on the top of the membrane using a micropipette. After the loading of the peptide, 500 μL of DMEM complete medium with L-glutamine, sodium pyruvate and 15% Fetal Bovine Serum was placed out of the insert. The peptide was let to self-assemble in the flow cabinet during 20 min. At this point the medium penetrates in the insert from the bottom membrane inducing a bottom-to-top self-assembly of RAD16-I inside the membrane. To wash out the remaining sucrose, medium was added in sequential steps on the top of the ensemble and allowed to infiltrate. Finally 500 μL were loaded inside the insert and 2.5 mL in the well outside the insert.

Results and Comments

Both, PEA100 and PEA90 membranes are filled with RAD16-I peptide. Each group consisted on 2 samples. It is therefore considered a composite material: elastomeric membranes+self-assembling peptides.

The results showed that PEA100 membrane allows RAD16-I to fill the porous easily than PEA90 membrane. Thus, it seems that the most hydrophobic PEA100 polymer is in principle preferable in order to obtain the combined system with improved mechanical properties compared with those of the peptide gel, that would permit to hold the heartbeat.

Example 6

The goal of this example is to show the viscoelasticity evaluation of elastomer matrix scaffolds for ventricular support and myocardial regeneration.

Viscoelastic properties of myocardial tissue has been recently identified as a major determinant of contraction and relaxation coupling. The goal of our approach is to develop tissue engineered implants for ventricular support and myocardial regeneration, using nanobiomaterials associated with stem cell grafting. In the present study viscoelastic properties of several nanobiopolymers developed were assessed by applying a constant stress. Their stress-strain responses as well as their temporal dependencies mimicked the behavior of the classical Kelvin Standard Linear Solid Model which combines a Voigt system (hookean spring $E_2$ in parallel with a viscous dashpot $n_2$), and a hookean spring ($E_1$) in series of the Voigt system. Thus, under a constant stress, the materials instantaneously deform to some strain, which is the elastic part of the strain, and after that it will continue to deform and asymptotically approach a steady-state strain. This last part is the viscous component of the strain.

Methods

We evaluated viscous and elastic properties of 3 types of porous membranes:

A) a non-degradable copolymer of ethyl acrylate and hydroxyethyl acrylate with a 90:10 mass ratio of monomers (PEA 90), B) partially degradable polymer: methacrylate-endcapped caprolactone (CLMA) membranes, and C) native collagen matrices of bovine origin (control group).

The elastic modulus $E_1$ and $E_2$ (in mN/mm) and the viscosity coefficient ($n_2$ in mN/mm·s) were calculated using the load clamp technique. Pieces of 12 mm×1 mm, thickness 1 mm of PEA 90 matrices were studied in water (8 days) (1), in water (1 hour) (2) or only in air (3); same protocol for CLMA matrices: (4), (5), (6); and same protocol for collagen matrices: (7), (8), (9).

Results

All samples showed linear stress-strain relationship, simplifying the evaluation of viscoelasticity. In all groups, $E_1$ ranged from 20 to 40 mN/mm, except in (6) where $E_1$ was about 180 mN/mm. In all groups, $E_2$ ranged from 10 to 100 mN/mm, except in (6) where $E_1$ was about 400 mN/mm. In all groups, $n_2$ ranged from 1 to 5 mN/mm·s, except in (6) where $n_2$ was about 18 mN/mm·s. All studied matrices exhibited a viscoelastic behavior similar to the Kelvin Standard Linear Solid Model. However, all viscoelastic coefficients $E_1$, $E_2$ and $n_2$ were higher in CLMA in air than in all other groups.

Conclusions

Viscous and elastic properties of "bioactive implants" of the present invention match the characteristics of myocardial contraction and relaxation activity at both structural and functional bio integrative levels. Bioactive implants specially conditioned for the recovery of left and/or right ventricular myocardium may reduce adverse chamber remodelling and fibrosis.

Example 7: Tensile Properties of Partially Degradable Polymer Matrices Employed for the Fabrication of the Membranes This example aims to give representative information about the swelling capacity and the tensile mechanical properties of three possible polymer compositions employed for the elastomer membrane fabrication, as a function of their weight fraction of degradable and non-degradable parts.

Polyethylacrylate (PEA) was chosen as the non-degradable polymer, and poly(caprolactonemethacryloyloxyethyl ester) (PCLMA) as the partially degradable polymer. Three systems containing both polymers were prepared by radical polymerization of the monomers in mass ratios of 15:85, 50:50 and 85:15 (see table). Sheets of the three bulk polymers of 0.3 mm thickness were obtained in this way, and samples of dimensions 0.3 mm×30 mm×6 mm were cut from those sheets in order to perform mechanical tests. The table gives, for each system prepared, the weight fraction of non-degradable part, of partially degradable component, and of degradable part.

Stress-strain measurements were made in tensile mode in a Microtest SCM3000 95 apparatus by stretching the specimen at a constant strain rate of 0.01/min and simultaneously measuring the force applied to the specimen. The tests were continued until the samples broke. The tests were carried out on samples equilibrated in phosphate buffer saline (PBS). At least 3 replicates of each sample were tested. The weight increase after 48 h immersion in PBS was referred to the dry weight of the sample to define the "swelling mass increase".

TABLE

Tensile and swelling properties of the three polymer matrices.

| System PEA:PCLMA mass ratio | mass ratio of degradable part (%) | mass ratio of non-degradable part (%) | mass ratio of partially degradable polymer (PCLMA) (%) | swelling mass increase (%) | breaking strength (KPa) | strain at break (%) | Young modulus (Pa) |
|---|---|---|---|---|---|---|---|
| 15:85 | 40.1 | 59.9 | 85 | 6.83-0.15 | 1982-117 | 19.8-1.8 | 11961-1295 |
| 50:50 | 23.6 | 76.4 | 50 | 5.32-0.13 | 1904-402 | 23.7-5.0 | 10214-1368 |
| 85:15 | 7.1 | 92.9 | 15 | 1.92-0.40 | 3445-299 | 55.8-0.8 | 9816-472 |

It is to be understood that the above-described embodiments are illustrative of only a few of the many possible specific embodiments, which can represent applications of the principles of the invention. Numerous and varied other arrangements can be readily devised in accordance with these principles by those skilled in the art without departing from the spirit and scope of the invention.

What is claimed is:

1. A method for treating a mammalian subject having injured myocardial tissue comprising the steps of:
implanting a bioactive implant scaffold at a site of the injured myocardial tissue, said scaffold including an elastomeric microporous membrane comprising at least one non-degradable polymer and at least one partially degradable polymer, a nanofiber hydrogel and cells, said membrane having a porosity comprised between 70% and 90%, the pores being interconnected and having diameters comprised between 50 microns and 500 microns, said non-degradable polymer is selected from the group consisting of polyethylacrylate and polyethylacrylate copolymerized with 10% wt or 20% wt hydroxyethylacrylate comonomer; said partially degradable polymer is selected from the group consisting of polycaprolactone, caprolactone 2-(methacryloyloxy)ethyl ester and caprolactone 2-(methacryloyloxy) ethyl ester copolymerized with ethylacrylate in weight proportions of this last comonomer comprised between 30% and 80%, the percentage of non-degradable polymers versus degradable polymers is comprised between 10% wt and 90% wt.

2. The method of claim 1 wherein the bioactive implant scaffold further comprises a helical loop band including one or more loops, said helical loop band being formed of a non-degradable or semi-degradable material.

3. The method of claim 2 wherein said helical loop band is integrated into the bioactive implant scaffold.

4. The method of claim 1 further comprising the step of:
fixing a helical loop band to said implanted bioactive implant scaffold, said helical loop band including one or more loops, said helical loop band being formed of a non-degradable or semi-degradable composite material.

5. The method of claim 1 wherein the bioactive implant scaffold is a patch for partially or completely wrap the left and/or right ventricle.

6. The method of claim 5 wherein the patch further includes a helical loop band integrated into the patch.

7. The method of claim 1 wherein the scaffold is positioned at the left and right ventricles, wherein the injured myocardial tissue is in the right and left ventricles.

8. The method of claim 1 wherein the scaffold further comprises a biodegradable portion, the biodegradable portion being formed of a biodegradable or semi-degradable material.

9. The method of claim 8 wherein the biodegradable or semi-degradable portion is positioned at the left ventricle, wherein the injured myocardial tissue is the right ventricle.

10. The method of claim 8 wherein the biodegradable or semi-degradable portion is positioned at the right ventricle, wherein the injured myocardial tissue is the left ventricle.

11. The method of claim 2 wherein the bioactive implant scaffold comprises a single helical loop band.

12. The method of claim 2 wherein the bioactive implant scaffold comprises a double helical loop band.

13. The method of claim 4 wherein the helical loop band is formed of the semi-degradable composite material.

14. The method of claim 4 wherein the semi-degradable composite material is polycaprolactone.

15. The method of claim 8 wherein the biodegradable portion is formed of a composite degradable and semi-degradable material.

16. The method of claim 8 wherein the biodegradable portion comprises polycaprolactone.

17. The method of claim 1, wherein the bioactive implant scaffold additionally comprises a system for the controlled release or absorbance of active molecules, said molecules being encapsulated in degradable micro-particles made of hyaluronic acid.

* * * * *